United States Patent [19]
Brenner et al.

[11] Patent Number: 4,753,106
[45] Date of Patent: Jun. 28, 1988

[54] STEAM QUALITY METER

[75] Inventors: Raul Brenner, Villa Park; John M. DiMartino, Chicago, both of Ill.

[73] Assignee: Kay-Ray, Inc., Arlington Heights, Ill.

[21] Appl. No.: 928,806

[22] Filed: Nov. 7, 1986

[51] Int. Cl.⁴ ............................................. G01N 25/60
[52] U.S. Cl. ...................... 73/29; 73/861.04; 374/42
[58] Field of Search ................. 73/29, 861.04, 861.02, 73/112; 366/340; 374/42

[56] References Cited

U.S. PATENT DOCUMENTS

| 2,332,624 | 10/1943 | Boeckeler | 366/341 |
| 3,430,483 | 3/1969 | Clawson et al. | 73/29 |
| 3,866,026 | 2/1975 | Febve de Vivy | 364/556 X |
| 4,334,783 | 6/1982 | Suzaka | 366/341 X |
| 4,542,993 | 9/1985 | Mims | 374/42 |
| 4,574,626 | 3/1986 | Kaya et al. | 374/31 X |
| 4,576,036 | 3/1986 | Huang et al. | 73/29 |
| 4,576,043 | 3/1986 | Nguyen | 73/861.04 X |
| 4,581,926 | 4/1986 | Moore et al. | 73/155 |
| 4,618,939 | 10/1986 | Davis | 364/558 X |

OTHER PUBLICATIONS

Measurement of Steam Quality, Mass Flow Rate, and Enthalpy Delivery Rate Using Combined Neutron Densitometer and Nozzel–by G. E. Woiceshyn, Petro-Canada Inc.; P. S. Yuen, Atomic Energy of Canada; H. John, Kernforschungszentrum; and J. J. Manzano-Ruis, INTEVEP S.A., 4/20/86, pp. 353–364, Society of Petroleum Engineers.

Primary Examiner—Daniel M. Yasich
Attorney, Agent, or Firm—Kinney & Lange

[57] ABSTRACT

A meter measures the quality of steam flowing in a conduit. The steam comprises a liquid and a vapor. The meter includes a mixer in the conduit for mixing the steam in the conduit to produce a mixture which has a density representative of the liquid and the vapor. A density sensor, or desitometer, senses the density of the mixture. The densitomer produces an improved output due to the mixing. A pressure sensor senses pressure in the steam line. A calculating means, such as a microprocessor system, calculates the steam quality as a function of the sensed density and pressure.

11 Claims, 1 Drawing Sheet

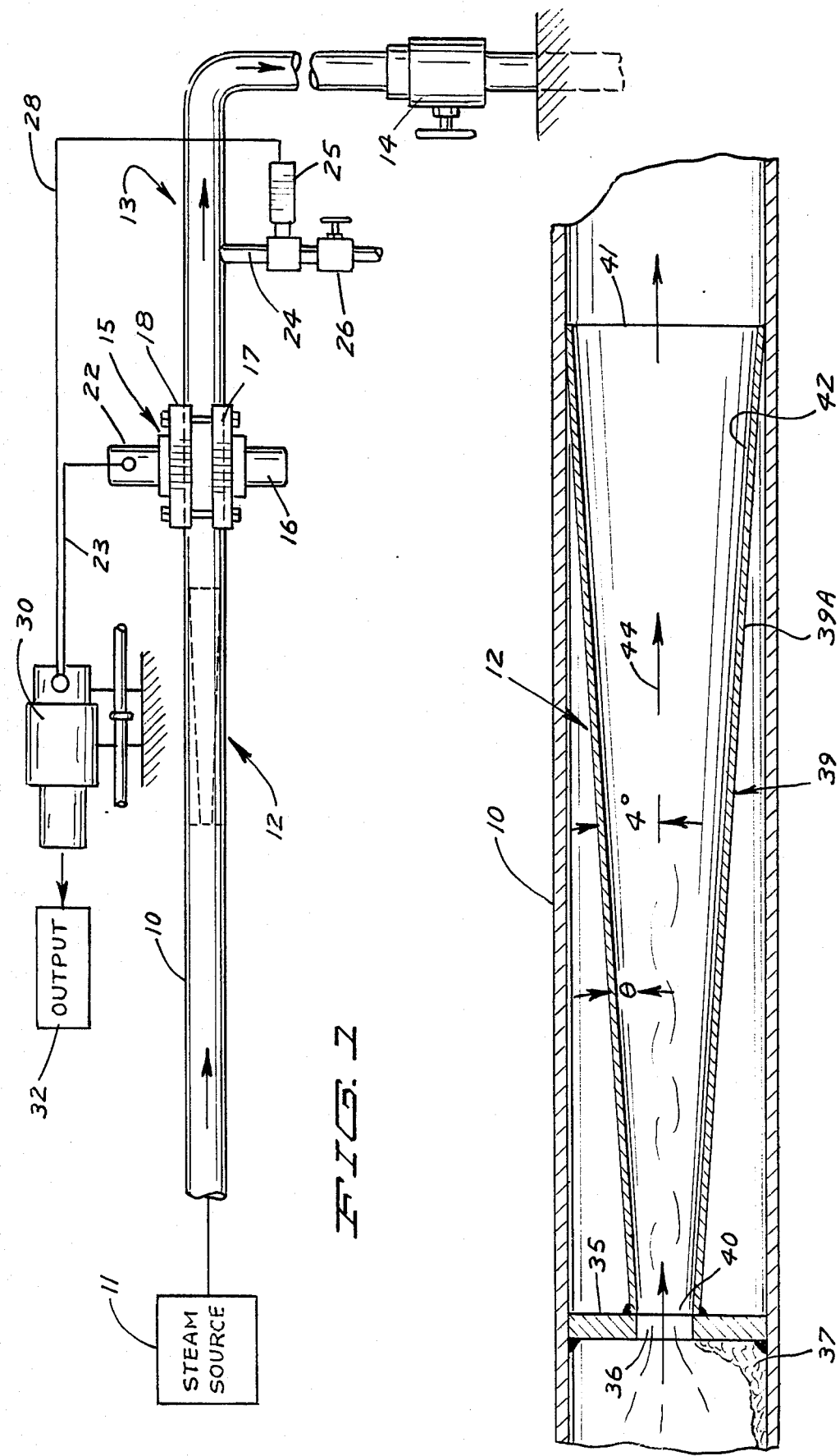

STEAM QUALITY METER

BACKGROUND OF THE INVENTION

1. Field of the Invention

The present invention relates to a system for measuring a parameter such as steam quality and to a mixer for mixing liquid and gaseous vapor in order to permit accurate measurement of steam quality.

2. Description of the Prior Art

Steam quality is a parameter used for many purposes in a wide variety of industries, including power generation, oil recovery, freeze protection, process heating, and the like. The mass ratio of dry steam to the total fluid mass within a steam sample is termed steam quality and is usually expressed as a percentage. The energy content of wet steam is dependent upon its "steam quality," and for this reason it is important to measure steam quality to determine the energy in the steam, which in turn determines the steam's ability to achieve a desired heating result. If steam quality is known, the rate of energy or power available from the steam to accomplish a particular job is capable of being determined.

In particular, in oil recovery systems, it has been known that injecting steam into wells drilled in the oil field will make the crude oil more flowable and will increase the output of the coil field. The measurement of the steam quality at particular locations immediately before being injected into a well head permits the operators to maximize the efficiency of the steam heating of the oil field, and in this way aid in efficient operation of the oil pumping system.

Particularly in oil fields, the steam sometimes is carried miles from the steam source, and during this travel time some condensation occurs. The liquid phase or droplets in the steam can be moving at a different flow rate than the vapor portion of the steam, creating difficulties in measuring the density of the steam. In particular, there can be condensed liquid moving along the bottom of a pipe.

Density measuring instruments using radiation have been used on steam, but with less than satisfactory results when the fluid is wet steam. Variations in the make-up of the steam such as different flow rates of the liquid and vapor phases affect the densitometer's output and thus conditioning of the steam is desired. Simple orifice plates have been used in an attempt to condition steam for density measurement, however results with wet steam have been unsatisfactory. In order to obtain steam quality information, the pressure and the density of the steam must be determined. Steam quality is determined according to the general equation:

$$\text{Steam Quality} = (Vs - Vl)/(Vv - Vl)$$

Where:
Vs = Specific volume of the steam.
Vl = Specific volume of the liquid portion.
Vv = Specific volume of the vapor portion.

The present invention solves the problems associated with ensuring that the liquid phase and the vapor phase of the steam are sufficiently homogenized so that sufficiently accurate density measurements can be obtained to permit an accurate calculation of steam quality.

An article entitled "Measurement of Steam Quality, Mass Flow Rate, and Enthalpy Delivery Rate using combined Neutron Densitometer and Nozzle," by G. E. Woiceshyn et al., was presented at the Society of Petroleum Engineers/Department of Energy, 5th Symposium on Enhanced Oil Recovery, held in Tulsa, Okla. in April, 1986, and published as paper SPE/DOE/4907, and is included herein by reference. This paper discusses the need for accurate measurement of steam quality at the well head for efficient operation and reliable evaluation of the recovery projects that utilize steam injection. This publication shows the use of neutron density detectors and associated equations for determining steam quality as well as other steam parameters.

Proper mixing in the region where density measurement is made is extremely important in solving the problems of varying flow rates and obtaining proper measurements of density over a wide range of flow rates at a fixed density measurement "window" or location on the pipe. In order to obtain proper mixing, it is desirable to have the steam flowing in a velocity range where the liquid phase can be well mixed with the vapor phase. Velocity can be increased by using a simple orifice plate in the steam pipe, but this technique can provide mixing over only a limited range of flow velocities, and the location downstream from the orifice where the proper mixture is obtained can vary undesirably with the flow rate. The orifice plate also has the disadvantage of creating a large pressure drop which, particularly on large lines, results in a large energy loss. Commercially available vane type mixers can reduce the pressure drop, but do not mix adequately over a normal range of flow velocities. These vane type mixers also have a substantial surface area against which water can collect, tending to minimize the mixing ability of the vane type mixer.

The effects of velocity of steam in the pipe are so varied or inconsistent that obtaining a homogeneous mixture of the two-phase flow (liquid and vapor) through a wide enough pressure and flow range to make a desired measurement with existing mixers is riddled with problems. Water can drop out, water can collect on the pipe walls, and there can be stratified flow at different parts of the pipe, and all of these problems can affect the measurements of density and steam quality. Thus the problems are substantial and a low cost, low pressure drop mixer that breaks up the water particles into small enough droplets to be carried at a reasonable velocity and which does not have the problems of separating water out of the steam flow before the density measurement is made is needed.

SUMMARY OF THE INVENTION

This invention relates to a system for measuring qualities of fluid mixtures flowing through a conduit such as a steam quality in a steam line. Mixing means are disposed in the conduit for mixing the fluid. The mixing means produce a mixture having a density representative of a density of the flowing mixture in the conduit. The mixture having a density representative of the density of the flowing mixture can be produced at a desired fixed location in the conduit. Density sensing means are disposed on the conduit and coupled to the mixed fluid for sensing the density of the mixed fluid. Pressure sensing means are coupled to the fluid in the conduit. The pressure sensing means sense a pressure of the fluid in the conduit. Calculating means are coupled to the density sensing means and the pressure sensing means. The calculating means calculate the quality as a function of the sensed density and the sensed pressure. The calculating means provide an output representative of the calculated quality. The density sensing means are spaced from the mixing means such that the density sensing means senses a selected mixture of fluid produced by the mixing means. The density sensing means thus provide an improved measure of the density of the fluid. Errors associated with density measurement of unmixed fluid are thus substantially avoided.

In a preferred embodiment, the fluid comprises a mixture of dry steam and liquid water, or wet steam; the calculating means provide an output representative of steam quality. In a further preferred embodiment, the mixing means comprise a diffuser disposed in the conduit and extending along the direction of fluid flow. The diffuser preferably comprises an inlet having an opening smaller than the conduit, an outlet, and a wall diverging from the inlet to the outlet for producing the desired mixture. The diffuser preferably provides a mixture emitted from the outlet wherein a liquid flow and a vapor flow in the fluid have substantially the same velocities. The density sensing means preferably comprise a radiation source disposed on the conduit for emitting radiation through the mixed fluid and a radiation sensor disposed on the conduit to receive a portion of the radiation which is representative of the density of the mixed fluid. Gamma radiation is preferred as the emitted radiation. Gamma radiation has a high level of interaction with steam which contains hydrogen. The radiation sensing means cooperates with the mixing means to provide a preferred accurate density measurement of a mixed sample of the fluid.

BRIEF DESCRIPTION OF THE DRAWINGS

FIG. 1 is a part schematic representation of a typical steam carrying pipe leading to a steam injection well head, with a steam mixer made according to the present invention shown installed therein in relation to the density detection instrumentation; and FIG. 2 is an enlarged sectional view of the steam carrying pipe showing a steam mixer made according to the present invention installed therein.

DETAILED DESCRIPTION OF THE PREFERRED EMBODIMENTS

A steam carrying pipe or conduit indicated generally at 10 carries steam flow from a steam source 11, that in oil field usages can be several miles upstream. The steam pipe 10 has a steam mixing section 12, in which the mixer of the present invention is installed. The output end 13 of the sampling section leads to a well head 14, for example, in an oil field, such as is explained in the prior art article mentioned in the prior art section of this specification. Detemination of how much energy is in the steam and thus the capability of the steam to carry out its intended function is based upon the steam quality adjacent to the well head. The steam density measuring instrumentation shown generally at 15 includes a gamma radiation source 16 mounted onto pipe saddle plates 17 and 18 which are clamped onto the pipe 10 in a suitable location immediately downstream of the steam mixing section 12 of the pipe. The radiation source 16 provides gamma radiation across the pipe 10 toward a radiation detector 22 of conventional design that provides an output along an output line 23 that is proportional to the density of the material flowing through the pipe 10 between the source 16 and the detector 22.

Additionally, a drain pipe or conduit 24 is provided in the pipe 10 downstream from the detector 22 and source 16. The drain pipe has a pressure sensor and transmitter 25 mounted therein in order to determine the pressure of the steam in the pipe section at the output side of the mixing section 12. A suitable drain valve 26 is provided in the drain conduit for emptying the steam pipe 10 to reference the zero steam density point on the density measuring instrumentation prior to start up.

An output signal line 28 from the pressure sensing transmitter provides an electrical signal that is proportional to the steam pressure, the signals of density and pressure are provided to a transmitter or processor 30 that combines these signals using an algorithm derived from steam tables to calculate and provide a steam quality output. This steam quality output is represented at 32. Determining the quality of the steam being carried determines what should be done to ensure optimum operation of the system, as shown, of the oil field in which well-head 14 is placed.

In order to have accurate steam quality measurements, it is essential that the density of the steam, including both the liquid and vapor phases, be determined accurately. In many instances where there is condensed water or the like along the sides of the steam pipe in the area where the density measurement instrumentation is positioned, the steam quality measurements are erroneous because the liquid and vapor phases are not uniform across the diameter of the pipe.

Various mixers have been advanced, but none that provide for low pressure drop and accurate mixing. The mixing section 12 of the pipe as shown in FIG. 2 includes an orifice plate 35 that is mounted across the pipe, and has an orifice throat or opening 36 in the center thereof. The size of the orifice opening 36 is selected so that even at low pressures and velocity, the liquid and vapor phases, including as well any condensed water or precipitate such as the water indicated at 37 in the lower portion of the throat (the pipe is horizontal, as shown), are carried into the central opening 36, and the velocity of the vapor phase of the steam is increased to a point where the liquid phase and water are broken up into droplets by the shear force of the vapor phase acting against the surface tension of the liquid phase and water to make the droplets very fine (mist-like), and which droplets are then suspended and carried by the vapor phase as the liquid phase and water pass through the opening or throat 36.

A diffuser indicated generally at 39 is provided on the outlet or downstream side of the orifice plate. The diffuser comprises an expanding, gentle, conically shaped tubular wall section 39A, and the diffuser 39 has a small or minor diameter end shown at 40 that is the same diameter as the diameter of the opening 36, and the wall 39A sealingly joins the orifice plate and increases in size in direction of flow to its major diameter or outlet diameter indicated at 41 that is positioned downstream a sufficient distance so that the angle of the wall relative to its central axis is preferably in the range of 4 degrees. This angle shown is shown at $\theta$ as illustrated in FIG. 2.

The diffuser 39 has a smooth interior surface 42 to provide a streamlined passageway to reduce the turbulence of the mixed steam passing therethrough, so that the liquid and vapor phases of the steam gradually decrease in velocity in downstream direction. Because the water droplets are reduced to a small enough size, the vapor will continue to keep the droplets suspended in a homogenized mix of liquid phase and vapor phase steam for subsequent density measurement.

It will be appreciated that the velocity increase which results from the flow restriction caused by the orifice plate 35 will have associated with it a pressure drop. The diffuser 39 coupled downstream of the orifice plate 35 not only gradually decreases the flow velocity but also advantageously recovers a substantial portion of the pressure drop. Moreover, the diffuser 39 causes a gradual dispersion of the homogenized mix through the conduit at the region where density measurement is to be made.

The flow direction, which is indicated at 44 thus is toward the major diameter 41, and the droplets will remain in homogeneous suspension as they pass through the density measuring region 15. The drain conduit is indicated at 24 as shown in FIG. 2, as well, and this is downstream of the density measuring location, but closely adjacent to it so that the pressure in the steam pipe at this location is measured.

The conical wall is not tortuous or twisted. The wall is smooth and provides the same cross-sectional slope at substantially any plane perpendicular to the axis of the diffuser. The diffuser cross-section, as shown, is circular, but could be other geometrical shapes so long as the walls taper gently and do not form turbulent flow regions.

The mixer thus is very low cost, efficient, and has no moving parts. It does ensure that the liquid or water phase of the steam is broken up into small enough droplets to be carried at the velocity of the steam at the full diameter of the pipe.

Although the present invention has been described with reference to preferred embodiments, workers skilled in the art will recognize that changes may be made in form and detail without departing from the spirit and scope of the invention.

While the invention has been described in terms of measuring two-phase flows having a liquid phase and a vapor or gas phase, the invention can be applied to two-phase flows comprising a liquid phase and a solid phase, two-phase flows comprising a vapor phase and a solid phase, and three-phase flows comprising a liquid phase, a vapor phase and a solid phase, wherein the solid phase comprises substantially particulate matter.

What is claimed is:

1. A meter for measuring the quality of steam flowing in a conduit having a conduit wall, the steam comprising liquid and vapor, the meter comprising:

mixing means disposed in the conduit for mixing the steam in the conduit to produce a mixture thereof having a density representative of the liquid and vapor flowing in the conduit, said mixing means including a diffuser for gradually decreasing the velocity of the mixture;

density sensing means coupled to the conduit for sensing the density of the mixture downstream from the diffuser such that the sensed density is an improved representation of steam density;

pressure sensing means coupled to the conduit for measuring a steam pressure in the conduit;

calculating means coupled to the density sensing means and pressure sensing means for calculating the steam quality as a function of the sensed density and pressure and for providing an output representative of steam quality.

2. The meter of claim 1 wherein a portion of the liquid flows substantially along the conduit wall and the mixing means mixes the liquid with the steam.

3. The meter of claim 1 wherein the mixing means includes means coupled to the fluid for accelerating the flow for mixing.

4. The meter of claim 3 wherein the mixing means introduces a pressure change along the conduit and the diffuser decelerates the mixed flow such that the pressure change is reduced.

5. The meter of claim 4 wherein the diffuser comprises means disposed in the conduit having an inlet substantially smaller than the conduit for receiving the flow, and having an outlet larger than the inlet and spaced away from the inlet for discharging the mixed flow, and having a wall diverging from the inlet to the outlet.

6. The meter of claim 5 wherein the wall defines a substantially smooth passageway diverging at an angle from the conduit axis such that the flow passes therethrough with a reduced turbulence.

7. The meter of claim 6 wherein the wall has a substantially frustoconical shape.

8. The meter of claim 7 wherein the angle is between one degree and ten degrees.

9. The meter of claim 8 wherein the angle is substantially four degrees.

10. The meter of claim 3 wherein the acceleration means comprises a flow restriction disposed in the conduit defining an opening therethrough for accelerating the fluid to a desired velocity.

11. An apparatus for mixing fluid flowing in a conduit, the fluid comprising a liquid phase and a vapor phase, the apparatus comprising:

restriction means disposed in the conduit for receiving the fluid and having an orifice therethrough for accelerating the fluid to a selected velocity for mixing the liquid phase and the vapor phase;

diffuser means disposed in the conduit and extending from the orifice to a diffuser opening spaced away from the orifice for diffusing the mixed fluid, the diffuser having a wall diverging from the orifice to the diffuser opening; and density sensing means disposed on the conduit for sensing the density of the mixture, the density sensing means sensing density in a selected region in the conduit spaced downstream from the diffuser opening such that the liquid and vapor phases are substantially mixed in the selected region over a range of fluid flow.

* * * * *